US012577514B2

(12) United States Patent
Koshi et al.

(10) Patent No.: US 12,577,514 B2
(45) Date of Patent: Mar. 17, 2026

(54) METHOD OF PRODUCING BIOCHIPS

(71) Applicant: Toray Industries, Inc., Tokyo (JP)

(72) Inventors: Yoichiro Koshi, Kamakura (JP);
Kunihisa Nagino, Kamakura (JP)

(73) Assignee: Toray Industries, Inc., Tokyo (JP)

( * ) Notice: Subject to any disclaimer, the term of this
patent is extended or adjusted under 35
U.S.C. 154(b) by 996 days.

(21) Appl. No.: 17/772,117

(22) PCT Filed: Oct. 28, 2020

(86) PCT No.: PCT/JP2020/040370
§ 371 (c)(1),
(2) Date: Apr. 26, 2022

(87) PCT Pub. No.: WO2021/085454
PCT Pub. Date: May 6, 2021

(65) Prior Publication Data
US 2022/0372415 A1     Nov. 24, 2022

(30) Foreign Application Priority Data

Oct. 29, 2019    (JP) .................................. 2019-196302

(51) Int. Cl.
*C12M 1/00*          (2006.01)
*C12N 15/09*         (2006.01)
(Continued)

(52) U.S. Cl.
CPC ............... *C12M 1/00* (2013.01); *C12N 15/09*
(2013.01); *C12Q 1/6837* (2013.01);
(Continued)

(58) Field of Classification Search
None
See application file for complete search history.

(56) References Cited

U.S. PATENT DOCUMENTS

2003/0170672 A1     9/2003   Cho et al.
2003/0175750 A1     9/2003   Barany et al.
(Continued)

FOREIGN PATENT DOCUMENTS

JE     2004-264289 A     9/2004
JP     2001-139532 A     5/2001
(Continued)

OTHER PUBLICATIONS

International Search Report dated Dec. 1, 2020, of corresponding
International Application No. PCT/JP2020/040370, along with an
English translation.

(Continued)

*Primary Examiner* — Heather Calamita
*Assistant Examiner* — Elizabeth Rose Lafave
(74) *Attorney, Agent, or Firm* — DLA Piper LLP (US)

(57) ABSTRACT

A method of biochip production includes a step A of
applying a solution containing a selective binding substance,
a salt, and a condensing agent to the surface of a substrate,
a step B of immobilizing the selective binding substance to
the surface of the substrate, a step C of drying the applied
solution to allow the salt in the solution to precipitate on the
surface of the substrate, and a step D of using an image
detection device to detect a precipitate of the salt formed in
the step C, wherein, in the step A, the condensing agent in
the solution has a concentration of not less than 30 mM and
not more than 80 mM.

10 Claims, 1 Drawing Sheet

Specification includes a Sequence Listing.

100

(51) Int. Cl.

| | |
|---|---|
| *C12Q 1/6837* | (2018.01) |
| *G01N 33/483* | (2006.01) |
| *G01N 33/543* | (2006.01) |
| *C12Q 1/68* | (2018.01) |

(52) U.S. Cl.

CPC ......... *G01N 33/483* (2013.01); *G01N 33/543* (2013.01); *C12Q 2527/125* (2013.01); *C12Q 2527/137* (2013.01)

(56) References Cited

U.S. PATENT DOCUMENTS

| | | | | |
|---|---|---|---|---|
| 2005/0064415 | A1 | 3/2005 | Shim | |
| 2014/0187724 | A1 | 7/2014 | Komatsu et al. | |
| 2015/0086992 | A1 | 3/2015 | Nitta | |
| 2018/0095067 | A1* | 4/2018 | Huff | G01N 33/48721 |
| 2021/0210416 | A1* | 7/2021 | Eisele | H01L 23/3735 |

FOREIGN PATENT DOCUMENTS

| | | | |
|---|---|---|---|
| JP | 2003-279576 | A | 10/2003 |
| JP | 2005-229934 | A | 9/2005 |
| JP | 2006-208012 | A | 8/2006 |
| JP | 2006-234712 | A | 9/2006 |
| JP | 2008-125439 | A | 6/2008 |
| JP | 2008-201782 | A | 9/2008 |
| JP | 2011-200230 | A | 10/2011 |
| JP | 2012-37363 | A | 2/2012 |
| JP | 2013-233126 | A | 11/2013 |
| WO | 2013/024694 | A1 | 2/2013 |

OTHER PUBLICATIONS

Eisen, M. B. et al., "DNA arrays for analysis of gene expression," *Methods in Enzymology*, 1999, vol. 303, pp. 179-205 (Summary).

* cited by examiner

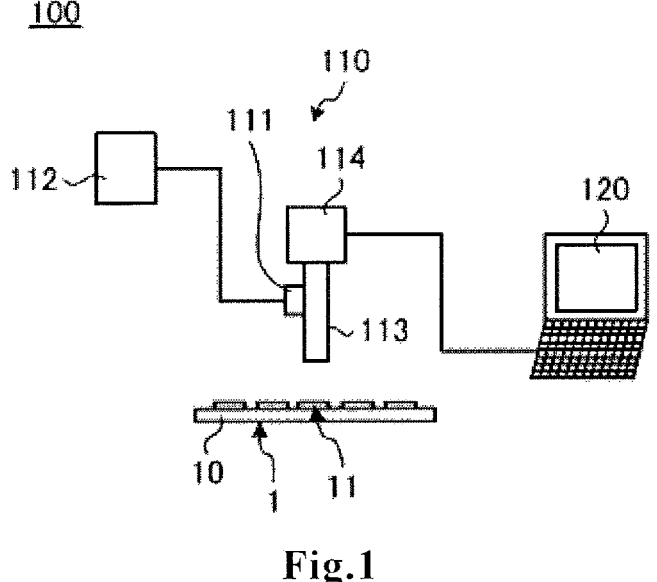
Fig.1
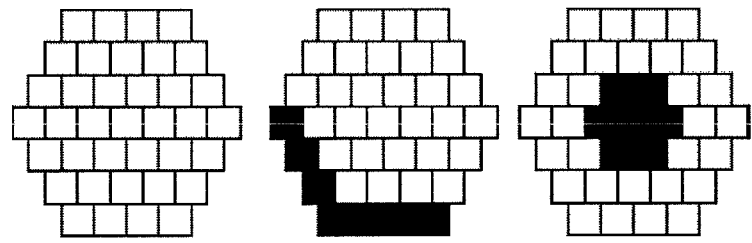
Fig.2
Fig.3

SEQUENCE LISTING

```
<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Synthetic Polynucleotides, 5'-end amino group

<400> SEQUENCE: 1
aactatacaa cctactacct ca                                              22
```

METHOD OF PRODUCING BIOCHIPS

TECHNICAL FIELD

This disclosure relates to a method of producing a biochip with a substance(s) immobilized on the surface of a substrate, wherein each substance ("selective binding substance") selectively binds to a target of analysis.

BACKGROUND

A biochip comprises a substrate (support) and a selective binding substance(s) such as nucleic acid or protein immobilized on the surface of the substrate, wherein each selective binding substance selectively binds to a target of analysis and the selective binding of the target is detected via a signal such as a fluorescence signal, and also wherein the intensity variation and/or the pattern of each signal may allow identification of a molecule and/or diagnosis of a disease.

As methods of biochip production, the Affymetrix method and the Stanford method are known, in the former of which each oligonucleotide is synthesized as a selective binding substance on the surface of a substrate by photolithography, and in the latter of which each pre-made solution containing a selective binding substance ("spotting solution") is applied to a substrate to immobilize the selective binding substance on the substrate. As a procedure of applying the spotting solution in the Stanford method, a method of using a metal pin to spot a spotting solution on a substrate or a method of using a dispenser or an inkjet device to discharge a spotting solution towards a substrate is known. However, contact failure between the tip of the pin and the substrate during spotting of the spotting solution, no discharge of the spotting solution due to clogging in a nozzle that discharges the spotting solution, or other troubles may cause spotting defects such as the absence of a spot of the spotting solution at a target position on the substrate. Thus, a method of inspecting the quality of each spot is important in the production of biochips to find and eliminate biochips with spotting defects as defective biochips, which maintains the quality of biochips.

As examples of the method of inspecting the quality of each spot, an inspection method utilizing a salt contained in a spotting solution, in which a precipitate of the salt is detected in each spot position by using an image taken by a laser scanner or the like after the spotting solution is spotted on the surface of a substrate (Michael B. Eisen, Patrick O. Brown, DNA arrays for analysis of gene expression, 1999, Methods Enzymol. 303, 179-205), and an inspection method based on a fluorescent substance, in which the fluorescence from the fluorescent substance is detected in each spot position after a spotting solution containing the fluorescent substance is spotted on the surface of a substrate (JP 2003-279576 A), are known. Among these methods, the method described in Michael B. Eisen, Patrick O. Brown, DNA arrays for analysis of gene expression, 1999, Methods Enzymol. 303, 179-205 advantageously requires no further reagent such as a fluorescent substance to be added in a spotting solution. In that method, a DNA molecule is non-covalently immobilized as a selective binding substance to a poly-L-lysine-coated substrate by electrostatic interaction. However, covalent bonding is generally preferred for stability when a selective binding substance is immobilized on the surface of a substrate.

In JP 2006-208012 A and JP 2011-200230 A, a method of covalently immobilizing a selective binding substance(s) to the surface of a substrate is described. Specifically, a substrate with carboxyl groups formed on its surface is used, and a spotting solution containing an aminated oligoDNA which is a selective binding substance, and a condensing agent is spotted on the surface of the substrate, and the selective binding substance is covalently immobilized on the substrate by an amide bond between the carboxyl group on the substrate and the amino group of the selective binding substance, which is formed through a condensation reaction. Compared to the method described in JP 2001-139532 A, in which a substrate whose carboxyl groups have been modified in advance into activated carboxylate ester groups is used to allow a selective binding substance in an applied spotting solution without a condensing agent to be immobilized, the method described above, in which a spotting solution that contains a condensing agent is used, is advantageously relieved from the necessity of the preliminary substrate activation and is also protected from being affected by degradation of the activated substrate during storage.

SEQUENCE LISTING

The Applicant hereby incorporates by reference the sequence listing contained in the ASCII text file titled SequenceListing.txt, created Apr. 22, 2022 and having 451 bytes of data.

SUMMARY

We employed the method described in JP 2006-208012 A to produce a substrate in which a selective binding substance was immobilized on the surface through a condensation reaction by using a spotting solution containing the selective binding substance, a salt and a condensing agent, and also employed the method described in Michael B. Eisen, Patrick O. Brown, DNA arrays for analysis of gene expression, 1999, Methods Enzymol. 303, 179-205 to test an inspection method based on precipitation of the salt to examine the quality of each spot deposited on the substrate, as shown in Comparative Example 1 below. However, the precipitation of the salt was not observed in each spot where the selective binding substance had been deposited so that spot inspection was not attained. This result indicates that a simple combination of the conventional methods is not sufficient to allow for the spot inspection when a selective binding substance is immobilized on the surface of a substrate by using a spotting solution containing a condensing agent.

We found that in the production of a biochip in accordance with the conventional method, in which a spotting solution containing a condensing agent described above was used for immobilization of a selective binding substance(s) to the surface of a substrate, the condensing agent contained in the spotting solution would inhibit precipitation of a salt and thus prevent the spot inspection based on the precipitation of the salt from being completed. We then found that a large change in the concentration of the condensing agent contained in the spotting solution from the conventionally used concentration induced the precipitation of the salt and allowed for the spot inspection.

We thus provide (1) to (5):

(1) A method of producing a biochip in which a selective binding substance(s) is/are immobilized on the surface of a substrate, the method comprising: a step A of applying a solution containing the selective binding substance, a salt, and a condensing agent to the surface of the substrate; a step B of immobilizing the selective binding substance to the surface of the substrate; a step C of drying the applied solution to allow the salt in the solution to precipitate on the surface of the substrate; and a step D of using an image detection device to detect a precipitate(s) of the salt formed in the step C, wherein, in the step A, the condensing agent in the solution has a concentration of not less than 30 mM and not more than 80 mM.

(2) The method of producing a biochip according to (1), wherein the condensing agent is soluble in water.

(3) The method of producing a biochip according to (1) or (2), wherein the condensing agent is a carbodiimide derivative.

(4) The method of producing a biochip according to (3), wherein the carbodiimide derivative is 1-(3-dimethyl-aminopropyl)-3-ethylcarbodiimide.

(5) The method of producing a biochip according to any of (1) to (4), wherein the selective binding substance is a nucleic acid.

Our method for the production of biochips, in which immobilization of a selective binding substance(s) to the surface of a substrate through a condensation reaction is achieved by using a spotting solution containing a condensing agent, allows for inspecting the quality of each spot based on the precipitation of a salt contained therein and for producing biochips with a certain quality level.

BRIEF DESCRIPTION OF THE DRAWINGS

FIG. 1 shows a configuration example of a spot detector system.

FIG. 2 shows schematic drawings obtained by binarization of images of appropriate spots where a spotting solution has been properly applied (3 examples).

FIG. 3 shows schematic drawings obtained by binarization of images of inappropriate spots where a spotting solution has been improperly applied (3 examples).

LIST OF REFERENCE NUMERALS 1 biochip
10 substrate
11 spot positions
100 spot detector system
110 image acquisition unit
111 light source
112 light source power supply
113 body tube
114 imaging device
120 analyzing unit

DETAILED DESCRIPTION

Our method produces a biochip in which a selective binding substance(s) is/are covalently immobilized on the surface of a substrate. The method comprises steps A to D:

(A) applying a solution (spotting solution) containing a selective binding substance, a salt, and a condensing agent to the surface of the substrate;

(B) immobilizing the selective binding substance to the surface of the substrate;

(C) drying the applied solution to allow the salt in the solution to precipitate on the surface of the substrate; and (D) using an image detection device to detect a precipitate of the salt formed in the step C.

Each of the above-described steps in the method will be described below.

Step A applies a solution (spotting solution) containing a selective binding substance, a salt, and a condensing agent to the surface of a substrate in a biochip.

The material of the substrate used for biochips is not limited to a specific material, provided that the material allows immobilization of a selective binding substance(s) to the substrate through a condensation reaction. The material may be, for example, any of resins, glass, metals, and silicon wafer and is preferably a resin from the viewpoint of convenience of surface treatment and mass production.

Examples of the resin, which is a material for the substrate, include polyacrylic acid esters, polymethacrylic acid esters, polycarbonate, polystyrene, polyvinyl acetate, and polyester resins, and polyacrylic acid esters and polymethacrylic acid esters are preferred as the material of the substrate. Among these, polymethacrylic acid ester polymers include, for example, poly(alkyl methacrylate) (PAMA) polymers such as poly(methyl methacrylate) (PMMA), poly(ethyl methacrylate) (PEMA), and poly(propyl methacrylate). PMMA is preferred.

Additionally, a known copolymer may also be used as the resin. Examples of the copolymer include styrene-acrylonitrile copolymers (AS resin), acrylonitrile/butadiene/styrene copolymers (ABS resin), and acrylonitrile/ethylene-propylene-diene/styrene copolymers (AES resin), and polymethacrylate-containing copolymers such as methyl methacrylate/acrylonitrile/butadiene/styrene copolymers (MABS resin), methyl methacrylate/butadiene/styrene copolymers (MBS resin), and methyl methacrylate/styrene copolymers (MS resin).

The shape of the substrate is not specifically limited, but commercially available glass slides or other flat substrates with a similar size are suitable for use. Additionally, substrates having a structure with protruded and recessed portions on the surface can be used for the purpose of increasing the sensitivity of detection (see, for example, JP 2004-264289 A). When a substrate with a surface having protruded and recessed portions is used, each selective binding substance is required to be immobilized correctly on the top surfaces of the protruded portions. Thus, the spot inspection has more importance than when using a flat substrate. Moreover, the substrate is preferred to have a surface colored in black or other colors and/or made of a material suitable for light absorption to reduce light reflection from the substrate during observation for the purpose of increasing the sensitivity of detection.

Each selective binding substance is immobilized on the surface of the substrate through a condensation reaction. Therefore, functional groups that allow the condensation reaction to proceed such as amino, hydroxy, thiol (sulfanyl), or carboxyl groups are preferred to exist on the surface of the substrate. Among these functional groups, carboxyl group is more preferred. To introduce functional groups of interest into the surface of a substrate, a method of introducing functional groups by using a silane coupling agent with such a functional group (for example, 3-aminopropyltriethoxysilane) can be used when the substrate used is a glass substrate. When the substrate used is a substrate made of a resin, a polymer with such a functional group may be applied on the surface of the substrate, or ester groups present on the surface of the substrate may be hydrolyzed into carboxyl groups by an alkaline hydrolysis reaction when the resin is an acrylic resin such as poly(methyl methacrylate) (PMMA).

The selective binding substance to be immobilized on a substrate refers to a substance that can selectively bind to a target of analysis in a direct or indirect manner, and representative examples of the selective binding substance include nucleic acids, proteins, saccharides, and other antigenic compounds. The nucleic acids may be PNA as well as DNA and RNA. A single-stranded nucleic acid with a particular nucleotide sequence binds to another single-stranded nucleic acid with a nucleotide sequence that is complementary to the whole length or a part of the nucleotide sequence via hybridization. Thus, single-stranded nucleic acids are considered as selective binding substances. Moreover, the proteins include antibodies, antigen-binding fragments derived from antibodies such as Fab and F(ab')$_2$ fragments, and various antigens. An antibody and antigen-binding fragments derived therefrom selectively bind to a corresponding antigen, while the antigen selectively binds to the corresponding antibody and antigen-binding fragments. Thus, these proteins are considered as selective binding substances. The saccharides are preferably polysaccharides and include various antigens. Antigenic materials other than proteins or saccharides may also be immobilized. Selective binding substances that can be used may be commercially available products or products isolated from living cells or the like. Nucleic acids are especially preferred as the selective binding substance. Among nucleic acids, nucleic acids with 10 to 100 nucleotides in length, which are called oligonucleic acids, are preferred because such nucleotides are easily and artificially synthesized by a synthesizer and are also easily modified to carry an amino group at an end thereof, which facilitates immobilization of the resulting nucleic acids on the surface of the substrate. Furthermore, nucleic acids with 20 to 100 nucleotides in length are more preferred from the viewpoint of stable hybridization. Preferably, the nucleic acids carry a functional group that allows the condensation reaction to proceed, namely an amino group, a hydroxy group, a thiol group, or a carboxyl group, particularly an amino group, at an end. Methods of attaching any of the functional groups to nucleic acids at an end are well known. For example, an amidite reagent containing an amino group can be attached to a nucleic acid at an end for the attachment of an amino group (see WO 2013/024694).

Each selective binding substance is immobilized on the surface of the substrate through a condensation reaction by using a condensing agent. The condensing agent is a reagent that promotes a condensation reaction to form an amide bond or an ester bond between the selective binding substance and a functional group present on the substrate. The condensing agent is added to a spotting solution to be used. The amide bond is preferred for the attachment of a selective binding substance to the surface of the substrate from the viewpoint of stability.

The condensing agent is added to a spotting solution together with a selective binding substance to be used. Thus, the condensing agent is preferably soluble in water. Examples of the water-soluble condensing agent include 1-(3-dimethylaminopropyl)-3-ethylcarbodiimide (also known as 1-ethyl-3-(3-dimethylaminopropyl)carbodiimide) (EDC) and 4-(4,6-dimethoxy-1,3,5-triazin-2-yl)-4-methyl-morpholinium chloride (DMT-MM).

Condensing agents include, for example, carbodiimide derivatives, uronium derivatives, and phosphonium derivatives, which are different in molecular structure, and carbodiimide derivatives are preferred because of high versatility. Each of the "derivatives" refers to a compound having the named structure or the group(s). Thus, the term "carbodiimide derivative" refers to a compound containing a carbodiimide (—N=C=N—) group. Examples of the carbodiimide derivatives include EDC and N,N'-dicyclohexylcarbodiimide (DCC), and EDC is especially preferred from the viewpoint of water solubility as described above. The EDC may be in the form of hydrochloric acid salt or in a salt-free form.

The concentration of the condensing agent in a spotting solution used in step A is not less than 30 mM, preferably not less than 40 mM, because a lower concentration of the condensing agent would not allow the condensation reaction of the selective binding substance to proceed well. Moreover, the concentration of the condensing agent is not more than 80 mM, preferably not more than 60 mM, because a higher concentration of the condensing agent would inhibit the precipitation of a salt which is an indicator for the spot inspection. The concentration of the condensing agent in the spotting solution is 30 mM to 80 mM, preferably 40 mM to 60 mM.

Each spotting solution used for step A contains a salt together with a selective binding substance and a condensing agent. A salt refers to a compound formed by a reaction between an acid and a base and is composed of the positive component (cation) from the base and the negative component (anion) from the acid. Examples of the cation that makes up the salt include sodium, potassium, lithium, magnesium, and calcium ions. Examples of the anion that makes up the salt include chloride, bromide, fluoride, iodide, sulfate, nitrate, nitrite, acetate, phosphate, and perchlorate ions. A salt used is constituted by the combination of a cation(s) with an anion(s). Preferred specific examples of the salt include lithium chloride, sodium chloride, potassium chloride, magnesium chloride, magnesium bromide, magnesium perchlorate, magnesium nitrate, magnesium nitrite, magnesium acetate, magnesium sulfate, sodium phosphate, and potassium phosphate, and the salt is more preferably sodium chloride.

The concentration of the salt contained in the spotting solution is preferably not less than 10 mM, more preferably not less than 40 mM, still more preferably not less than 80 mM, because a too low concentration of the salt does not give a sufficient amount of the precipitation of the salt. Moreover, the concentration of the salt is preferably not more than 500 mM, more preferably not more than 120 mM, because a too high concentration of the salt could inhibit the reaction for the immobilization of the selective binding substance. The concentration of the salt in the spotting solution is preferably 10 mM to 500 mM, more preferably 40 mM to 120 mM, still more preferably 80 mM to 120 mM.

The concentration of a selective binding substance in the spotting solution is not specifically limited, provided that the selective binding substance can detect a target of analysis, and the concentration of the selective binding substance can be selected as appropriate. For example, when the selective binding substance is a nucleic acid, the concentration of the nucleic acid in the spotting solution is usually around 5 μM to 100 μM, preferably around 10 μM to 30 μM.

Preferably, the spotting solution containing the selective binding substance, the condensing agent, and the salt is an aqueous solution. Moreover, the spotting solution may contain other materials other than the selective binding substance, the salt, and the condensing agent such as an organic solvent, a surfactant, and a buffer for pH adjustment.

The procedure of applying the spotting solution to the surface of the substrate in step A is not limited to a specific method, and a method of spotting the spotting solution by using a pin or a method of discharging the spotting solution towards the substrate by using a dispenser or an inkjet device can be used to apply the spotting solution. Specifically, the method of spotting the spotting solution by using a pin comprises applying the spotting solution to the tip of the pin, and bringing the applied spotting solution into contact with the substrate to leave the spotting solution on the substrate.

Step B immobilizes the selective binding substance on the surface of the substrate. In step B, the condensing agent used allows a condensation reaction to proceed between the selective binding substance and functional groups on the surface of the substrate under normal conditions where the condensation reaction proceeds. Example conditions for the condensation reaction preferably include a temperature of 30° C. or higher, at which the condensation reaction is promoted, a humidity of 80% or higher, which is a humidity to prevent evaporation of the applied spotting solution, and a time period of 1 hour or longer. On the other hand, the temperature for the condensation reaction is preferably not higher than 60° C. because a too high temperature may cause degeneration of the selective binding substance or interfering of the condensation reaction. The upper limit of the time of the condensation reaction is not specifically limited, but the upper limit time is usually not longer than 48 hours, preferably not longer than 24 hours, because a too long period of time is meaningless. In a specific example, the substrate on which the spotting solution has been applied can be placed in a plastic container containing a small volume of water and then left to stand at 37° C. for 12 hours to immobilize the selective binding substance to the surface of the substrate.

Step C dries the spotting solution applied to the surface of the substrate until the salt contained in the solution precipitates on the surface of the substrate. No special conditions are required for drying the spotting solution because only a tiny volume of the spotting solution is deposited in each spot on the surface of the substrate. The temperature, humidity, and time for drying are not specifically limited, but preferred conditions for accelerated drying include a temperature of 18° C. or higher, a humidity of 80% or lower, and a time period of 10 minutes or longer. In contrast, a too high temperature may cause degeneration of the selective binding substance; therefore, the temperature is preferably not more than 50° C. In addition, the upper limit of the time of the drying is not specifically limited, but the upper limit time is usually not longer than 24 hours, preferably not longer than 2 hours, because a too long period of time is meaningless. In a specific example, the substrate on which the selective binding substance has been immobilized can be left to stand in the atmosphere at a temperature of 23° C. and a humidity of 50% for 30 minutes to dry the spotting solution and thereby to precipitate the salt.

Step D detects the precipitate of the salt formed in step C by using an image detection device. As the image detection device used for detection of salt precipitates, a laser scanner for use in microarray analysis and a spot detector system as shown in FIG. 1 can be used as well as a conventional light microscope or digital microscope.

Examples of the laser scanner that can be used for the detection of the salt precipitates include 3D-GENE® Scanner (Toray Industries, Inc.), SureScan™ microarray scanner (Agilent Technologies Inc.), and GenePix® microarray scanner (Filgen Inc.).

The spot detector system 100 shown in FIG. 1 comprises an image acquisition unit 110 for acquiring an image of a biochip 1 and an analyzing unit 120 for analyzing the image acquired by the image acquisition unit 110. A not shown controller controls the operations of the individual units of the spot detector system 100.

For the biochip 1, a spotting solution is spotted at spot positions 11 on a substrate 10.

The image acquisition unit 110 comprises a light source 111, a light source power supply 112, a body tube 113, and an imaging device 114.

The light source 111 is constituted by using an LED, a laser light source, a halogen lamp or the like. Illumination light is produced when the light source power supply 112 provides electricity to the light source 111. The illumination light emitting from the light source 111 passes into the body tube 113.

The body tube 113 comprises an objective lens, a relay lens and the like, which passes the illumination light from the light source 111 to the analytical chip 1 and collects the light reflected from the analytical chip 1 and guides the light to an imaging device 114.

The imaging device 114 receives light entering the body tube 113 and converts the light into electrical signals. The imaging device 114 outputs the converted electrical signals to the analyzing unit 120. The imaging device 114 is constituted by using a CMOS (Complementary Metal Oxide Semiconductor) image sensor, a CCD (Charge Coupled Device) image sensor, a photomultiplier tube (PMT) and the like.

For example, the analyzing unit 120 produces an image of the analytical chip 1 on the basis of the electrical signals generated by the imaging device 114 and converts the image into a binary image to evaluate the deposition of the spotting solution in each spot. The analyzing unit 120 is constituted by using a general-purpose processor such as CPU (Central Processing Unit), a specialized processor such as GPU (Graphics Processing Unit), a programmable logic device such as FPGA (field-programmable gate array), a display, an input device (such as keyboard) and the like.

The quality of each spot can be evaluated based on the presence or absence of a precipitate of the salt in each spot position by analyzing the obtained image data of the substrate or visually inspecting the substrate.

The analysis of the image data can be performed on a binarized image of the substrate. For example, an image of the substrate is binarized at a predetermined first threshold of the brightness of the image of the substrate to produce a binary image. In this binary image, white color is assigned to the areas where the salt has precipitated, and black color is assigned to the areas where no precipitation of the salt has occurred. A numerical value is assigned to each spot based on the binary image. The area corresponding to each spot is extracted from the binary image, and the number of pixels to which the color white is assigned (the number of white pixels) in the area is counted. Then, the quality of the spot is determined by comparing the counted number of white pixels with a predetermined second threshold. For example, when the number of white pixels is equal to or larger than the threshold, as shown in each example in FIG. 2, the spot is evaluated as a good spot (OK) where the spotting solution has been deposited appropriately. On the other hand, when the number of white pixels is less than the threshold, as shown in each example in FIG. 3, the spot is evaluated as a bad spot (NG) where the spotting solution has not been deposited appropriately.

The produced biochip may be tested by a known technique to determine whether a sufficient amount of the selective binding substance is immobilized or not. When a nucleic acid is used as a selective binding substance, a method of using a terminal deoxynucleotidyl transferase (TdT) as described, for example, in JP 2006-234712 A is available to measure the amount of the immobilized selective binding substance. In the TdT-based method, a drop of a solution containing TdT and a fluorochrome-labeled nucleotide is placed on the biochip to add the fluorochrome-labeled nucleotide to the terminus of the immobilized nucleic acid, and the biochip is washed and then subjected to measurement of fluorescence intensity using a laser scanner, by which the amount of the immobilized selective binding substance can be analyzed.

EXAMPLES

Example 1

(1) Substrate Production

A flat plate (75 mm×25 mm×1 mm) made of poly(methyl methacrylate) (PMMA) was immersed in an aqueous solution of 10 N sodium hydroxide at 70° C. for 15 hours and then washed sequentially with pure water, an aqueous solution of 0.1 N HCl, and pure water. This treatment resulted in hydrolysis of side chains on the surface of the PMMA substrate and formation of carboxyl groups.

(2) Deposition of Probe Solution (Step A)

A DNA with a nucleotide sequence of SEQ ID NO: 1 below was synthesized as a probe DNA:

5'-AACTATACAACCTACTACCTCA-3' (SEQ ID NO: 1, 23 nucleotides in length, aminated at the 5' end).

The DNA was dissolved in pure water to a concentration of 100 μM to prepare a stock solution. The stock solution was diluted 5-fold with a solution containing 1-ethyl-3-(3-dimethylaminopropyl)carbodiimide (EDC) as a condensing agent and sodium chloride as a salt to prepare spotting solutions. In the spotting solutions, the final concentration of EDC was 30 mM (Conditions 1 to 3), 40 mM (Conditions 4 to 6), 60 mM (Conditions 7 to 9), or 80 mM (Conditions 10 to 12), and the final concentration of sodium chloride was 40 mM (Conditions 1, 4, 7, and 10), 80 mM (Conditions 2, 5, 8, and 11), or 120 mM (Conditions 3, 6, 9, and 12). Aliquots of 40 μL were withdrawn from each of the spotting solutions and were spotted in the center of the above prepared substrate by using a spotting robot (GTMAS-Stamp-2; Japan Laser Corporation) to form 100 spots in a 10×10 grid.

(3) Immobilization of Probe DNA (Step B)

The substrate with the spotted probe solution of the above (2) was placed in a sealed plastic container and incubated at a temperature of 37° C. and a humidity of 100% for 20 hours to allow a condensation reaction to proceed and thereby to immobilize the probe DNA to the surface of the substrate.

(4) Drying of Spotting Solution and Precipitation of Salt (Step C)

The substrate was taken from the sealed plastic container of the above (3) and left to stand in the atmosphere at a temperature of 23° C. and a humidity of 50% for 30 minutes to dry the spotting solution on the surface of the substrate and thereby to precipitate the salt.

(5) Spot Detection (Step D) and Evaluation of Spot Quality

While the substrate with the dried spotting solution of the above (4) was irradiated by blue LED light, an image of the surface of the substrate was acquired using a CMOS camera (2M resolution, 2048×1088 pixels) with a telecentric lens (optical magnification: 2 times, WD: 66.7). The acquired image of the substrate was stored in a PC that was connected to the camera via USB, and the image data of the substrate was binarized. In the binarized image, white color was assigned to spotted areas where the salt precipitated, and black color was assigned to the spotted areas where no precipitation of the salt occurred. The area corresponding to each spot was extracted from the binary image, and the number of pixels to which the color white was assigned (the number of white pixels) in the area was counted. For all the spots, a spot with a ratio of white pixels of not less than 80% was evaluated as "excellent in the spot inspection" (a condition suitable for the inspection); a spot with a ratio of white pixels of not less than 50% and less than 80% was evaluated as "acceptable in the spot inspection" (a condition in which inspection is possible); a spot with a ratio of white pixels of less than 50% was evaluated as "unacceptable in the spot inspection" (a condition in which inspection is impossible). The results of the evaluations are shown in Table 1. After the spot inspection, the substrate was washed with pure water.

(6) Measurement of the Amount of Immobilized Probe DNA

A reaction solution was prepared by adding 10 U of a terminal deoxynucleotidyl transferase (TdT; manufactured by Takara Bio Inc.) to 250 μL of the included buffer (TdT Buffer) in which Cy3-labeled dUTP nucleotide (manufactured by GE Healthcare) was dissolved to a final concentration of 1 μM. A 50-μL drop of the reaction solution was placed on the substrate, and a cover slip was placed over the drop of the reaction solution, and the substrate was then placed in a plastic container and incubated at a temperature of 35° C. and a humidity of 100% for 1 hour. After the incubation, the cover slip was removed, and the substrate was washed and then dried. Each substrate used for the reaction was mounted on a "3D-GENE"® Scanner (Toray Industries, Inc.) and analyzed with excitation by a laser at 532 nm with an output power of 100% in the configuration of PMT30 to obtain signal intensity values from all the spots. Each substrate was evaluated to be "good in probe immobilization" (a condition that provides a sufficient amount of the immobilized probe DNA) when the signal intensities of all the spots were not less than 15,000; and evaluated to be "poor in probe immobilization" (a condition that provides an insufficient amount of the immobilized probe DNA) when there was a spot whose signal intensity was less than 15,000. The results are shown in Table 1.

Comparative Example 1

After a substrate was produced by the same method as described in the section (1) of Example 1, a probe solution was applied to the substrate by the same method as described in the section (2) of Example 1 except that a phosphate-buffered saline (137 mM sodium chloride, 2.7 mM potassium chloride, 10 mM disodium hydrogen phosphate, 1.76 mM potassium dihydrogen phosphate, pH 7.4) containing the DNA used in the section (2) of Example 1 at 30 μM and EDC at 260 mM (Condition 13) was used as a spotting solution in accordance with the method described in JP 2006-208012 A. In addition, the immobilization of the probe DNA, the drying of the spotting solution, the precipitation of the salts, the detection of spots, the evaluation of spot quality, and the measurement of the amount of immobilized probe DNA were performed by the same methods as described in the sections (3) to (6) of Example 1. The results are shown in Table 1.

Comparative Example 2

After a substrate was produced by the same method as described in the section (1) of Example 1, a probe solution was applied to the substrate by the same method as described in the section (2) of Example 1 except that a solution containing the DNA used in the section (2) of Example 1 at 20 μM, EDC at 20 mM, and sodium chloride at 40 mM (Condition 14), 80 mM (Condition 15), or 120 mM (Condition 16) was used as a spotting solution. In addition, the immobilization of the probe DNA, the drying of the spotting solution, the precipitation of the salt, the detection of spots, the evaluation of spot quality, and the measurement of the amount of immobilized probe DNA were performed by the same methods as described in the sections (3) to (6) of Example 1. The results are shown in Table 1.

Comparative Example 3

After a substrate was produced by the same method as described in the section (1) of Example 1, a probe solution was applied to the substrate by the same method as described in the section (2) of Example 1 except that a solution containing the DNA used in the section (2) of Example 1 at 20 μM, EDC at 90 mM, and sodium chloride at 40 mM (Condition 17), 80 mM (Condition 18), or 120 mM (Condition 19) was used as a spotting solution. In addition, the immobilization of the probe DNA, the drying of the spotting solution, the precipitation of the salt, the detection of spots, the evaluation of spot quality, and the measurement of the amount of immobilized probe DNA were performed by the same methods as described in the sections (3) to (6) of Example 1. The results are shown in Table 1.

TABLE 1

| | | Composition of a spotting solution | | Evaluation | Evaluation |
|---|---|---|---|---|---|
| | | Condensing agent concentration | Salt concentration | results of spot inspection | results of probe immobilization |
| Example 1 | Condition 1 | EDC, 30 mM | NaCl, 40 mM | Acceptable | Good |
| | Condition 2 | EDC, 30 mM | NaCl, 80 mM | Acceptable | Good |
| | Condition 3 | EDC, 30 mM | NaCl, 120 mM | Acceptable | Good |
| | Condition 4 | EDC, 40 mM | NaCl, 40 mM | Acceptable | Good |
| | Condition 5 | EDC, 40 mM | NaCl, 80 mM | Excellent | Good |
| | Condition 6 | EDC, 40 mM | NaCl, 120 mM | Excellent | Good |
| | Condition 7 | EDC, 60 mM | NaCl, 40 mM | Acceptable | Good |
| | Condition 8 | EDC, 60 mM | NaCl, 80 mM | Excellent | Good |
| | Condition 9 | EDC, 60 mM | NaCl, 120 mM | Excellent | Good |
| | Condition 10 | EDC, 80 mM | NaCl, 40 mM | Acceptable | Good |
| | Condition 11 | EDC, 80 mM | NaCl, 80 mM | Acceptable | Good |
| | Condition 12 | EDC, 80 mM | NaCl, 120 mM | Acceptable | Good |
| Comp. Example 1 | Condition 13 | EDC, 260 mM | NaCl, 137 mM KCl, 2.7 mM Na$_2$HPO$_4$, 10 mM KH$_2$PO$_4$, 1.76 mM | Unacceptable | Good |
| Comp. Example 2 | Condition 14 | EDC, 20 mM | NaCl, 40 mM | Acceptable | Poor |
| | Condition 15 | EDC, 20 mM | NaCl, 80 mM | Acceptable | Poor |
| | Condition 16 | EDC, 20 mM | NaCl, 120 mM | Acceptable | Poor |
| Comp. Example 3 | Condition 17 | EDC, 90 mM | NaCl, 40 mM | Unacceptable | Good |
| | Condition 18 | EDC, 90 mM | NaCl, 80 mM | Unacceptable | Good |
| | Condition 19 | EDC, 90 mM | NaCl, 120 mM | Unacceptable | Good |

In each of the conditions in Example 1, where the concentration of EDC which is a condensing agent, was 30 mM, 40 mM, 60 mM, or 80 mM, precipitation of the salt was observed to be appropriate for the spot inspection, and immobilization of a sufficient amount of the probe was also observed. Thus, these conditions were found to be biochip production conditions suitable for the spot inspection based on the precipitation of a salt. Among these conditions, the conditions where the concentration of EDC was 40 mM or 60 mM and the concentration of sodium chloride was 80 mM or 120 mM (Conditions 5, 6, 8, and 9) were found to be more suitable for the spot inspection because better precipitation of the salt was obtained.

In the condition of Comparative Example 1, where the concentration of EDC which is a condensing agent, was 260 mM similarly to the biochip production condition described in JP 2006-208012 A, precipitation of the salts was observed to be inappropriate for the spot inspection, which indicated that the spot inspection based on the precipitation of a salt was impossible under the condition. Also in one of the conditions of Comparative Example 3, where the concentration of EDC which is a condensing agent, was 90 mM, precipitation of the salt was likewise observed to be inappropriate for the spot inspection, which indicated that the spot inspection based on precipitation of a salt was impossible under the condition. A possible reason for no observation of salt precipitation under these conditions is explained by the hygroscopic property of EDC which is a condensing agent, that causes deliquescence to occur even after the spotting solutions are dried and consequently inhibits the precipitation of the salt(s).

In one of the conditions of Comparative Example 2, where the concentration of EDC which is a condensing agent, was 20 mM, although precipitation of the salt was observed to be appropriate for the spot inspection, the amount of the immobilized probe was insufficient, which indicated that the condition was not appropriate for the biochip production. This is considered to be caused by the low concentration of the condensing agent, which results in failure of the probe DNA to be immobilized on the substrate.

Accordingly, the results indicated that a concentration of not less than 30 mM and not more than 80 mM was preferred as the concentration of the condensing agent contained in the spotting solution.

The invention claimed is:

1. A method of producing a biochip in which a selective binding substance(s) is/are immobilized on a surface of a non-semiconductor substrate plate, the method comprising:

spotting a solution containing the selective binding substance, a salt, and a condensing agent on the surface of the non-semiconductor substrate plate;

immobilizing the selective binding substance to the surface of the non-semiconductor substrate plate;

drying the applied solution to allow the salt in the solution to precipitate on the surface of the non-semiconductor substrate plate; and detecting a precipitate(s) of the salt formed on the surface of the non-semiconductor substrate plate with an image detection device, wherein the condensing agent in the solution applied to the surface of the non-semiconductor substrate plate has concentration of not less than 30 mM and not more than 80 mM.

2. The method of producing a biochip according to claim 1, wherein the condensing agent is soluble in water.

3. The method of producing a biochip according to claim 1, wherein the condensing agent is a carbodiimide derivative.

4. The method of producing a biochip according to claim 3, wherein the carbodiimide derivative is 1-(3-dimethylaminopropyl)-3-ethylcarbodiimide.

5. The method of producing a biochip according to claim 1, wherein the selective binding substance is a nucleic acid.

6. The method of producing a biochip according to claim 2, wherein the condensing agent is a carbodiimide derivative.

7. The method of producing a biochip according to claim 6, wherein the carbodiimide derivative is 1-(3-dimethylaminopropyl)-3-ethylcarbodiimide.

8. The method of producing a biochip according to claim 2, wherein the selective binding substance is a nucleic acid.

9. The method of producing a biochip according to claim 3, wherein the selective binding substance is a nucleic acid.

10. The method of producing a biochip according to claim 4, wherein the selective binding substance is a nucleic acid.

\* \* \* \* \*